US00PP32540P2

(12) United States Plant Patent
Hooper

(10) Patent No.: US PP32,540 P2
(45) Date of Patent: Dec. 1, 2020

(54) ***MAGNOLIA* PLANT NAMED 'MGMIG2007'**

(50) Latin Name: ***Magnolia* hybrid**
Varietal Denomination: MGMIG2007

(71) Applicant: Vance James Hooper, Waitara (NZ)

(72) Inventor: Vance James Hooper, Waitara (NZ)

( * ) Notice: Subject to any disclaimer, the term of this patent is extended or adjusted under 35 U.S.C. 154(b) by 0 days.

(21) Appl. No.: 16/873,147

(22) Filed: Feb. 13, 2020

(51) Int. Cl.
*A01H 5/00* (2018.01)
*A01H 6/00* (2018.01)

(52) U.S. Cl.
USPC ..... Plt./223

(58) Field of Classification Search
USPC ..... Plt./223
See application file for complete search history.

*Primary Examiner* — Susan McCormick Ewoldt

(57) ABSTRACT

A new cultivar of *Magnolia* plant named 'MGMIG2007' that is characterized by a rounded bush shape, small leaves, upright cup shaped flowers having red-purple tepals, slender dark green branches with short internodes and moderate quantities of flowers during the Summer.

2 Drawing Sheets

Botanical classification: *Magnolia* hybrid.
Variety denomination: 'MGMIG2007'.

BACKGROUND OF THE INVENTION

The present invention relates to a new and distinct cultivar of *Magnolia* plant botanically known as *Magnolia* hybrid and hereinafter referred to by the cultivar name 'MGMIG2007'.

The new cultivar is the product of a breeding program conducted by the inventor in a cultivated area of Waitara, New Zealand. The objective of the breeding program is to develop new *Magnolia* cultivars that are smaller in size and have attractive flower colors.

'MGMIG2007' originated from crossing the female or seed parent an unnamed *Magnolia* cultivar and the male or pollen parent *Magnolia soulangeana* x *lilliflora* 'Genie' (U.S. Plant Pat. No. 20,748). The crossing was conducted in 2003 in a controlled environment. The cultivar 'MGMIG2007' was selected by the inventor in 2008 as a single plant within the progeny of the stated cross in a cultivated area of Waitara, New Zealand.

Asexual reproduction of the new cultivar 'MGMIG2007' by field budding was first performed in 2008 in Waitara, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Magnolia* cultivar 'MGMIG2007'. These traits in combination distinguish 'MGMIG2007' as a new and distinct cultivar.

1. *Magnolia* 'MGMIG2007' exhibits a rounded bush shape.
2. *Magnolia* 'MGMIG2007' exhibits small leaves.
3. *Magnolia* 'MGMIG2007' exhibits upright cup shaped flowers having red-purple tepals.

4. *Magnolia* 'MGMIG2007' exhibits slender dark green branches with short internodes.
5. *Magnolia* 'MGMIG2007' exhibits flower production during the Summer in a moderate quantity.

The closest comparison variety is *Magnolia* 'Mini Mouse' (not patented). 'MGMIG2007' is different than 'Mini Mouse' in the following characteristics:

1. *Magnolia* 'MGMIG2007' exhibits a rounded bush shape. In contrast, 'Mini Mouse' has an upright bush shape.
2. *Magnolia* 'MGMIG2007' exhibits small leaves. In contrast, the leaves of 'Mini Mouse' are larger.
3. *Magnolia* 'MGMIG2007' exhibits upright cup shaped flowers having red-purple tepals. In contrast, the flowers of 'Mini Mouse' are elongated in shape and purple-pink in color.
4. *Magnolia* 'MGMIG2007' exhibits short internodes. In contrast, the internodes of 'Mini Mouse' are longer.
5. *Magnolia* 'MGMIG2007' exhibits flower production during the Summer in a moderate quantity. In contrast, 'Mini Mouse' produces very few flowers during the Summer.

'MGMIG2007' is different than the female parent plant in the following characteristics:

1. *Magnolia* 'MGMIG2007' exhibits a rounded bush shape. In contrast, the female parent plant has a tree shape.
2. *Magnolia* 'MGMIG2007' exhibits small leaves. In contrast, the leaves of the female parent plant are larger.
3. *Magnolia* 'MGMIG2007' exhibits slender branches and short internodes. In contrast, the branches of the female parent plant are thicker and the internodes are longer.
4. *Magnolia* 'MGMIG2007' exhibits upright cup shaped flowers having red-purple tepals. In contrast, the flowers of the female parent plant have an open cup and saucer shape.

'MGMIG2007' is different than the male parent plant in the following characteristics:

1. *Magnolia* 'MGMIG2007' exhibits upright cup shaped flowers having red-purple tepals. In contrast, the flowers of the male parent plant are less cup shaped, more spreading and have red tepals.

2. *Magnolia* 'MGMIG2007' exhibits short internodes. In contrast, the internodes of the male parent plant are longer.
3. *Magnolia* 'MGMIG2007' exhibits flower production during the Summer in a moderate quantity. In contrast, the male parent plant produces fewer flowers during the Summer.

BRIEF DESCRIPTION OF THE DRAWING

The accompanying photographs illustrate the distinguishing traits of *Magnolia* 'MGMIG2007'.

The photograph of FIG. 1 shows an overall view of a 3 year old plant in flower.

Figure 1:
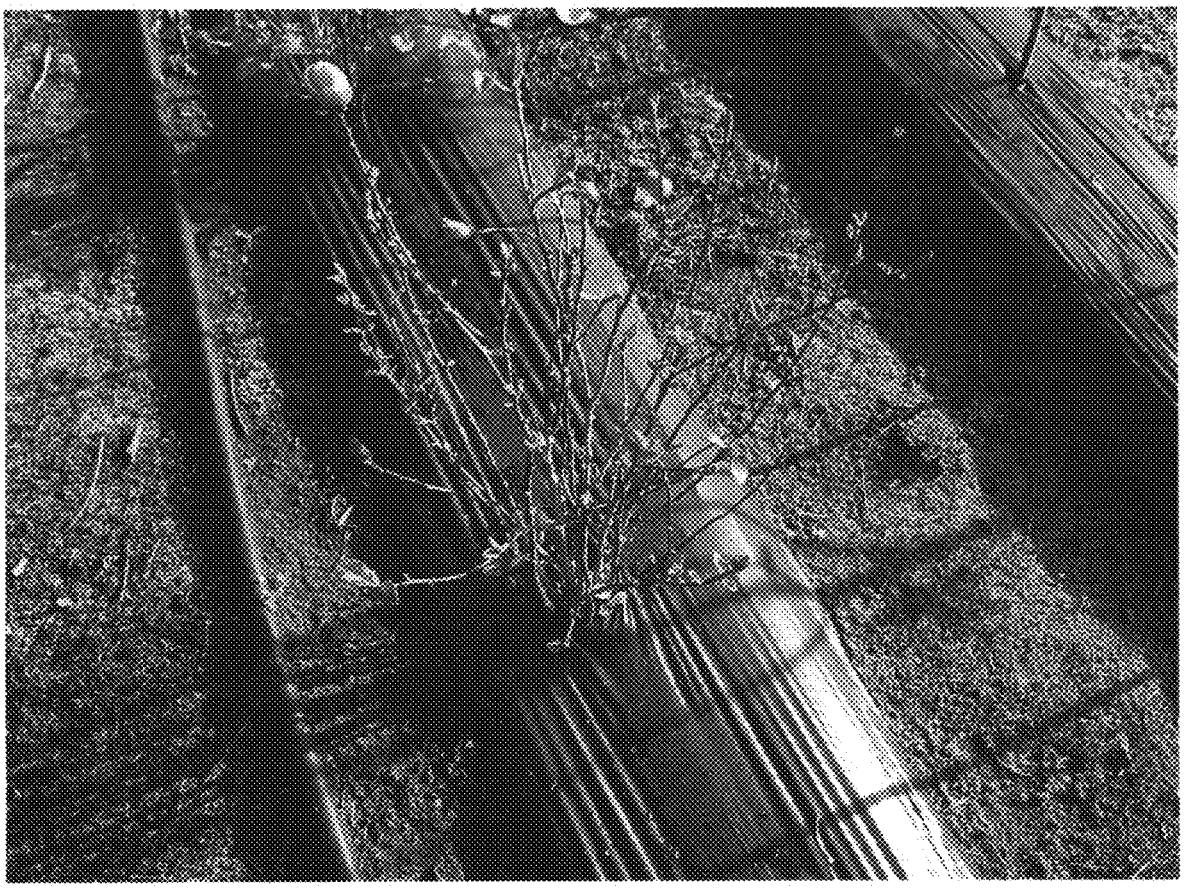
Figure 2:
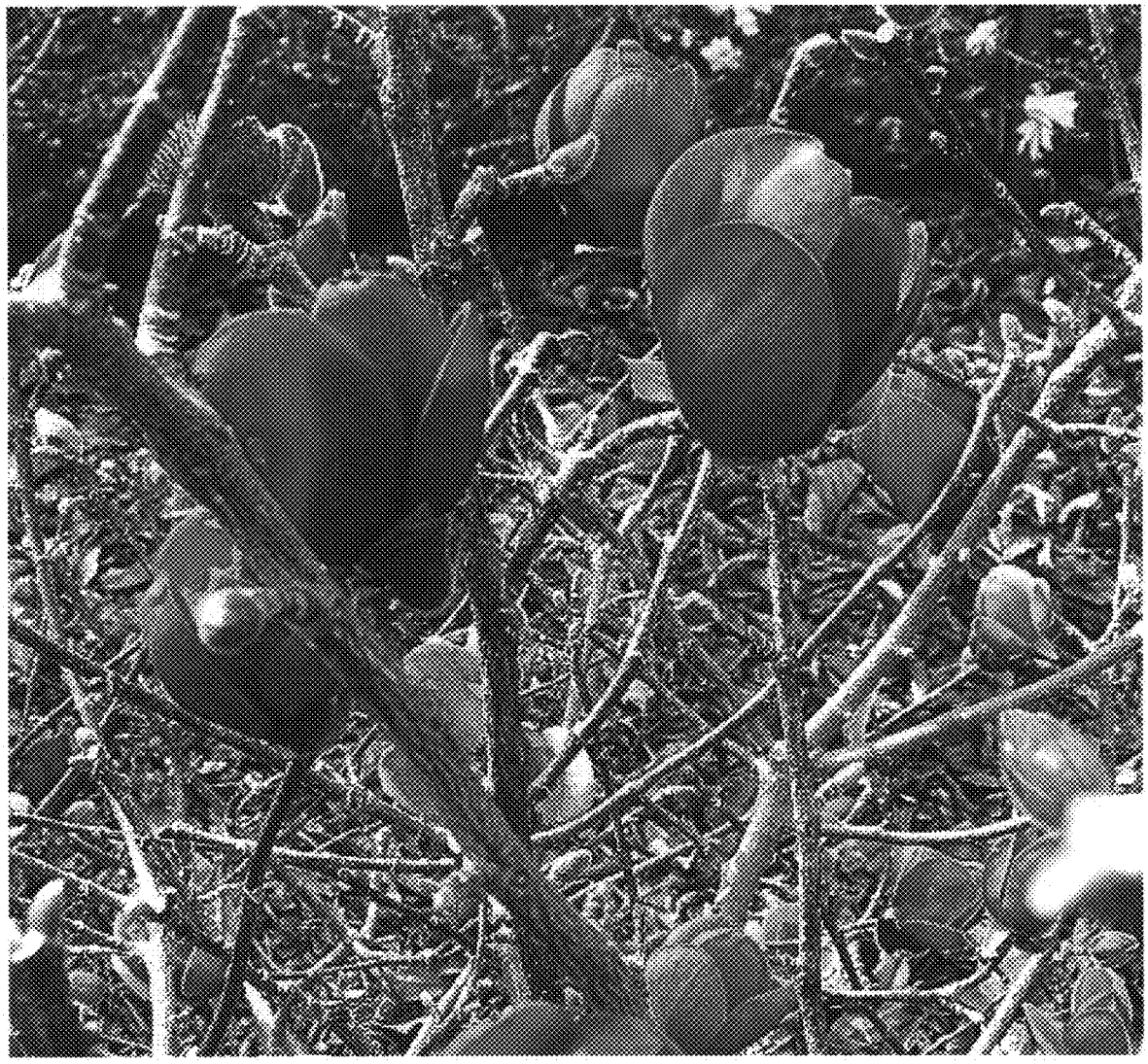

The photograph of FIG. 2 shows a close-up view of the flowers.

The photographs were taken using conventional techniques and although colors may appear different from actual colors due to light reflectance it is as accurate as possible by conventional photographic techniques.

BOTANICAL DESCRIPTION OF THE PLANT

The following is a detailed description of the new *Magnolia* cultivar named 'MGMIG2007'. Data was collected in Waitara, New Zealand from 2 year old field grown plants. The time of year was Spring and the average temperature was 15° Centigrade during the day and 9° Centigrade at night. Color determinations are in accordance with The Royal Horticultural Society Colour Chart 2015 edition, except where general color terms of ordinary dictionary significance are used. The growing requirements are similar to the species. 'MGMIG2007' has not been tested under all possible conditions and phenotypic differences may be observed with variations in environmental, climatic, and cultural conditions, however, without any variance in genotype.

Botanical classification: *Magnolia* hybrid 'MGMIG2007'.
Use: Ornamental.
Parentage: 'MGMIG2007' originated from the crossing of the female or seed parent an unnamed *Magnolia* cultivar and the male or pollen parent *Magnolia* 'Genie'.
Container size: 10 liter.
Vigor: Moderate.
Plant type: Perennial bush.
Growth habit: Upright, compact.
Plant shape: Rounded to pyramidal.
Height: 30.0 to 50.0 cm. in height.
Width: 30.0 cm. in width.
Growth rate: 40.0 cm. per year in first year, slower rate after flowers produced.
Hardiness: −15° to 35° C.
Propagation: Field budding, tissue culture and cuttings.
Crop time: 1 year from grafting.
Root: Fine and fibrous.
Stem:
- *Branching habit.*—Primary branching upward from center with laterals 30 degrees from horizontal.
- *Basal branching.*—Yes.
- *Number of lateral branches.*—3 to 5.
- *Lateral branch diameter.*—3 to 5 mm. in diameter.
- *Lateral branch length.*—15 to 35 cm. in length.
- *Internode length.*—12 to 20 mm. between nodes.
- *Stem color.*—NN137A to NN137B.
- *Stem aspect.*—Upward and outward.
- *Pubescence.*—Fine hairs are sparsely present.
- *Stem shape.*—Round.
- *Stem texture.*—Smooth.
- *Stem strength.*—Moderate.
- *Pinching.*—Once in early Summer.

Foliage:
- *Leaf arrangement.*—Alternate.
- *Compound or single.*—Single.
- *Quantity of leaves per lateral branch.*—7 to 10.
- *Leaf shape.*—Ovate.
- *Leaf apex.*—Cuspidate to acuminate.
- *Leaf base.*—Acute to cuneate.
- *Leaf length.*—50.0 to 70.0 mm. in length.
- *Leaf width.*—20.0 to 38.0 mm. in width.
- *Pubescence.*—Absent on upper surface, fine hairs on middle vein of lower surface.
- *Leaf texture.*—Both surfaces slightly leathery.
- *Leaf luster.*—Dull on both surfaces.
- *Leaf margin.*—Entire.
- *Vein pattern.*—Pinnate.
- *Young leaf color (upper surface).*—146A to 146B.
- *Young leaf color (lower surface).*—146B.
- *Mature leaf color (upper surface).*—147A.
- *Mature leaf color (lower surface).*—NN137B to NN137C.
- *Vein color (upper surface).*—147B.
- *Vein color (lower surface).*—NN137B.
- *Leaf attachment.*—Petiolate.
- *Petiole dimensions.*—8 to 13 mm. in length and 1.5 to 3 mm. in diameter.
- *Petiole color.*—N119A to N119B.
- *Durability of foliage to stress.*—High, resistant to wind damage and sunburn.

Flower:
- *Flower arrangement.*—Solitary terminal cup shaped flowers held upright.
- *Quantity of flowers per lateral stem.*—1.
- *Quantity of flower buds per lateral stem.*—1.
- *Quantity of flowers and buds per plant.*—Approximately 8.
- *Flowering habit.*—Flowers bloom in Spring before foliage appears and mid to late Summer with foliage.
- *Flowering season.*—Spring and mid to late Summer.
- *Time to flower or response time.*—5 to 7 weeks after breaking dormancy.
- *Fragrance.*—Very light scent.
- *Self-cleaning or persistent.*—Self cleaning.
- *Flower bud length.*—15 to 20 mm. in length.
- *Flower bud diameter.*—8 to 10 mm. in diameter.
- *Flower bud shape.*—Ovate.
- *Rate of bud opening.*—10 to 14 days.
- *Bud color.*—N79B to N79C.
- *Flower aspect.*—Upright.
- *Flower shape.*—Round cup shaped.
- *Flower dimensions.*—5 to 8 cm. in diameter and 4 to 6 cm. in height.
- *Flower longevity.*—Lasts approximately 6 to 9 days on plant.
- *Tepal arrangement.*—Whorls of three.
- *Number of tepals.*—6.
- *Fused or unfused.*—Not fused.
- *Tepal shape.*—Obovate.
- *Tepal margin.*—Entire.
- *Tepal apex.*—Rounded with slight notch.

*Tepal base*.—Rounded.
*Tepal texture*.—Smooth both surfaces.
*Tepal luster*.—Slightly glossy both surfaces.
*Tepal dimensions*.—3.5 to 6.0 cm. in length and 3.0 to 4.0 cm. in width.
*Tepal color when opening* (*upper side*).—74B to 74C.
*Tepal color when opening* (*under side*).—71A to 71B.
*Tepal color when fully opened* (*upper side*).—75B.
*Tepal color when fully opened* (*under side*).—71B to 71C.
*Tepal color fading to*.—N74B.

Sepals:
*Sepal appearance*.—Reflexed downward.
*Number of sepals*.—3.
*Sepal dimensions*.—11 to 22 mm. in length and 6 to 12 mm. in width.
*Sepal shape*.—Narrow Cordate.
*Sepal tip*.—Acute.
*Sepal base*.—Cuneate.
*Sepal margin*.—Entire.
*Sepal color immature*.—Upper side 138B to 138C, lower side 138A to 138B.
*Sepal color mature*.—Both sides N144A to N144B.

Peduncle:
*Peduncle dimensions*.—4 to 7 mm. in length and 4 to 8 mm. in diameter.
*Peduncle angle*.—Vertical.
*Peduncle strength*.—Moderately strong.
*Peduncle color*.—138A suffused N77A.

Reproduction organs:
*Stamen number*.—94 to 100.
*Anther shape*.—Curved upward.
*Anther length*.—7 mm. in length.
*Anther color*.—N79A with N79C stripe on base.
*Amount of pollen*.—Low.
*Pollen color*.—4D.
*Pistil number*.—54 to 60 in number.
*Pistil length*.—15 mm.
*Stigma shape*.—Curved upward.
*Stigma color*.—64A.
*Ovary color*.—187A.

Fruit and seed production has not been observed to date.
Disease and pest resistance has not been observed to date.

The invention claimed is:

1. A new and distinct variety of *Magnolia* plant named 'MGMIG2007' as described and illustrated.

* * * * *